United States Patent
Tseng et al.

(10) Patent No.: US 9,442,120 B2
(45) Date of Patent: *Sep. 13, 2016

(54) BIOMARKERS ASSOCIATED WITH NEPHROPATHY

(71) Applicant: Industrial Technology Research Institute, Hsin Chu (TW)

(72) Inventors: Tzu-Ling Tseng, Xinzhuang (TW); Ching-Fang Lu, Zhubei (TW); Wei-Ya Lin, Dali (TW); Tsai-Wei Hsu, Miaoli County (TW); Mary Ya-Ping Yeh, Taipei (TW); Yi-Ting Chen, Taoyuan County (TW); Chwei-Shiun Yang, Taipei (TW)

(73) Assignee: Industrial Technology Research Institute, Hsin-Chu (TW)

( * ) Notice: Subject to any disclaimer, the term of this patent is extended or adjusted under 35 U.S.C. 154(b) by 578 days.

This patent is subject to a terminal disclaimer.

(21) Appl. No.: 13/912,531

(22) Filed: Jun. 7, 2013

(65) Prior Publication Data

US 2013/0266976 A1   Oct. 10, 2013

Related U.S. Application Data

(63) Continuation of application No. 12/969,731, filed on Dec. 16, 2010, now Pat. No. 8,470,547, which is a continuation of application No. 12/694,639, filed on Jan. 27, 2010, now abandoned.

(60) Provisional application No. 61/147,785, filed on Jan. 28, 2009.

(51) Int. Cl.
| | |
|---|---|
| *G01N 33/68* | (2006.01) |
| *C07K 14/705* | (2006.01) |
| *C07K 16/28* | (2006.01) |

(52) U.S. Cl.
CPC ..... *G01N 33/6893* (2013.01); *C07K 14/70503* (2013.01); *C07K 16/2803* (2013.01); *G01N 2333/4728* (2013.01); *G01N 2333/70503* (2013.01); *G01N 2800/347* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 4,640,909 | A | 2/1987 | Ramsden et al. |
| 6,447,989 | B1 | 9/2002 | Comper |
| 6,479,638 | B1 | 11/2002 | Adema et al. |
| 6,664,385 | B1 | 12/2003 | Sanicola-Nadel et al. |
| 6,682,917 | B1 | 1/2004 | Nakamura et al. |
| 7,993,832 | B2 | 8/2011 | Rosenberg et al. |
| 8,465,980 | B2 * | 6/2013 | Lin .............. G01N 33/6893 |
| | | | 436/501 |
| 8,476,077 | B2 * | 7/2013 | Lin .............. G01N 33/6893 |
| | | | 436/501 |
| 2002/0110799 | A1 | 8/2002 | Comper |
| 2004/0009901 | A1 | 1/2004 | Holmdahl et al. |
| 2005/0191664 | A1 | 9/2005 | Comper |
| 2006/0166277 | A1 | 7/2006 | Karumanchi et al. |
| 2008/0124752 | A1 | 5/2008 | Ryals et al. |
| 2008/0187944 | A1 | 8/2008 | Allam et al. |
| 2009/0030037 | A1 | 1/2009 | Gurney et al. |

FOREIGN PATENT DOCUMENTS

| | | |
|---|---|---|
| WO | 98/24906 | 6/1998 |
| WO | WO 2004/005544 | 1/2004 |
| WO | WO 2007/102736 | 9/2007 |
| WO | WO2007124419 | 11/2007 |
| WO | 2008/021290 | 2/2008 |
| WO | WO2008021431 | 2/2008 |
| WO | WO2008141285 | 11/2008 |

OTHER PUBLICATIONS

Suzuki et al., "Initial Validation of a Novel Protein Biomarker Panel for Active Pediatric Lupus Nephritis" Pediatric Research 65(5):530-536 (2009).
Christiansen et al. "Increased urinary orosomucoid excretion is not related to impaired renal function in patients with type 2 diabetes", Journal of Diabetes and Its Complications 24 (2010) 28-36, available online Sep. 25, 2008.
Jain et al.; "Proteomic Analysis of Urinary Protein Markers for Accurate Prediction of Diabetic Kidney Disorder"; J. Assoc. Physician India; 53:513-520 (2005).
Jiang et al. "Increased urinary excretion of orosomucoid is a risk predictor of diabetic nephropathy" Nephrology 2009; 14, 332-337.
Varghese et al. "Urine biomarkers predict the cause of glomerular disease" J. Am. Soc. Nephrol. 2007; 18, 913-922.
Sharma et al. "The urine proteome as a biomarker of radiation injury" Proteomics Clin. Appl. 2008; 2, 1065-1086.
Lebbink et al. "The soluble leukocyte-associated ig-like receptor (LAIR)-2 antagonized the collagen/LAIR-1 inhibitory immune interaction" Journal of Immunology 2008; 180,1662-1669.
Das et al.; "Biomarkers for Renal Disease in Childhood"; Curr. Rheumatol Rep. 11(3):218-225 (2009).
Romao et al.; "Positive Acute-Phase Inflammatory Markers in Different Stages of Chronic Kidney Disease"; Am J. Nephrol. 26(1):59-66 (2006).
Kuby et al. Immunology, W.H. Freeman and Company (1992), p. 125.
Coca et al., "Biomarkers for the diagnosis and risk stratification of acute kidney injury: A systematic review" *Kidney International*, 73: 1008-1016 (2008).

(Continued)

*Primary Examiner* — Christine Foster
(74) *Attorney, Agent, or Firm* — Cesari and McKenna, LLP

(57) ABSTRACT

Use of urine biomarkers for diagnosing nephropathy, monitoring nephropathy progress, and assessing efficacy of a nephropathy treatment. These urine biomarkers include leukocyte-associated Ig-like receptor-2, alpha-1 acid glycoprotein, their fragments, and combinations thereof.

4 Claims, 2 Drawing Sheets

(56) References Cited

OTHER PUBLICATIONS

Ouyang et al., "Establishment of an ELISA system for determining soluble LAIR-1 levels in sera of patients with HFRS and kidney transplant" *Journal of Immunological Methods*, 292: 109-117 (2004).

National Center for Biotechnology Information ("*Homo sapiens* leukocyte-associated immunoglobulin-like receptor 2 (LAIR2), transcript variant 1, mRNA", NCBI Reference Sequence: NM_002288.3, Jul. 2007, retrieved from http://www.ncbi.nlm.nih.gov/nuccore/32481203?sat=12&satkey=1710068 on Jan. 16, 2013, and accompanying revision history (four pages total).

National Center for Biotechnology Information (NCBI), entry for NCBI Reference Sequence: NP_067154.1 (leukocyte-associated immunoglobulin-like receptor 2 isoform b precursor [*Homo sapiens*]), retrieved from http://www.ncbi.nlm.nih.gov/protein/NP_067154.1 on Oct. 25, 2012 (3 pages).

National Center for Biotechnology Information (NCBI), entry for PDB: 2OTP_B (Chain B, Crystal Structure of Immunoglobulin-Like Transcript 1 (IltLIR7LILRA2)), retrieved from http://www.ncbi.nlm.nih.gov/protein/168177057 on Oct. 25, 2012 (2 pages).

IEDB Analysis Resource, "ElliPro: Antibody Epitope Prediction", available at http://tools.immuneepitope.org/tools/ElliPro/iedb_input, 2012 (2 pages).

Harlow, E. and Lane, D., Antibodies: A Laboratory Manual (1988) Cold Spring Harbor Laboratory Press, Cold Spring Harbor, NY, pp. 72-76.

Wolfe, S.L., Molecular and Cellular Biology, 1993, pp. 790-793.

\* cited by examiner

```
SEQUENCE LISTING

<160> NUMBER OF SEQ ID NOS: 2

<210> SEQ ID NO 1
<211> LENGTH: 22
<212> TYPE: PRT
<213> ORGANISM: Artificial Sequence
<220> FEATURE:
<223> OTHER INFORMATION: fragment of leukocyte-associated Ig-like
      receptor-2

<400> SEQUENCE: 1

Asp Phe Leu Glu Leu Leu Val Lys Gly Thr Val Pro Gly Thr Glu Ala
1               5                   10                  15

Ser Gly Phe Asp Ala Pro
            20

<210> SEQ ID NO 2
<211> LENGTH: 32
<212> TYPE: PRT
<213> ORGANISM: Artificial Sequence
<220> FEATURE:
<223> OTHER INFORMATION: fragment of alpha-1 acid glycoprotein

<400> SEQUENCE: 2

Gly Gln Glu His Phe Ala His Leu Leu Ile Leu Arg Asp Thr Lys Thr
1               5                   10                  15

Tyr Met Leu Ala Phe Asp Val Asn Asp Glu Lys Asn Trp Gly Leu Ser
            20                  25                  30
```

BIOMARKERS ASSOCIATED WITH NEPHROPATHY

RELATED APPLICATIONS

This application is a continuation of U.S. application Ser. No. 12/969,731, filed on Dec. 16, 2010, which is a continuation of U.S. application Ser. No. 12/694,639, filed on Jan. 27, 2010, which claims priority to U.S. Provisional Application No. 61/147,785, filed on Jan. 28, 2009. The contents of all prior applications are hereby incorporated by reference in their entireties.

BACKGROUND OF THE INVENTION

Nephropathy, commonly known as kidney damage, is caused by, among others, diabetes, high blood pressure, drug toxicity, and inflammation.

Typically, nephropathy is diagnosed by determining the level of proteinuria (e.g., the level of urine albumin), or by examining the glomerular filtration rate (GFR), an indicator of renal function. Both approaches are not suitable for detecting early stage nephropathy, which typically displays no symptoms. While nephropathy can also be detected by renal biopsy, this invasive procedure is not an ideal diagnostic approach.

It is of great importance to develop a method for detecting early stage nephropathy. The key to achieving this goal is to identify reliable biomarkers associated with incipient nephropathy.

SUMMARY OF THE INVENTION

The present invention is based on unexpected discoveries that the urine levels of leukocyte-associated Ig-like receptor-2, alpha-1 acid glycoprotein, and fragments of these two proteins are significantly higher in a nephropathy patient than in a nephropathy-free patient. These protein molecules are therefore reliable biomarkers for diagnosis of early stage nephropathy.

Accordingly, one aspect of this invention features a nephropathy diagnostic method. This method includes at least the following steps: (a) obtaining a urine sample from a subject suspected of having nephropathy, (b) determining in the urine sample a level of a biomarker, and (c) assessing whether the subject has nephropathy based on the level of the biomarker. The biomarker used in the just-described method is one of the following: (i) leukocyte-associated Ig-like receptor-2 or a fragment thereof having at least ten amino acid residues, such as DFLELLVKGTVPGTEAS-GFDAP (SEQ ID NO:1), (ii) a fragment of alpha-1 acid glycoprotein having at least ten amino acid residues, such as GQEHFAHLLILRDTKTYMLAFDVNDEKNWGLS (SEQ ID NO:2), (iii) a combination of (i) and (ii), or (iv) a combination of (i) and alpha-1 acid glycoprotein.

An increase in the level of one of the four biomarkers, as compared to that in a nephropathy-free subject, indicates that the subject has nephropathy. In one example, the biomarker level is determined by a mass spectrometry assay (e.g., MALDI-MS, LC-MS, and LC-MS/MS). In another example, it is determined by an immune assay (e.g., ELISA, Western blot, RIA, FIA and LIA).

The above-described nephropathy diagnostic method is applicable to both humans and laboratory animals, e.g., those free of proteinuria. The term "a laboratory animal" used herein refers to a vertebrate animal commonly used in animal testing, e.g., mouse, rat, rabbit, cat, dog, pig, and non-human primate.

Another aspect of this invention features a method for monitoring nephropathy progress in a subject. This method includes (a) obtaining a first urine sample from a subject suffering from nephropathy (e.g., a human or a laboratory animal), (b) determining in the first urine sample a level of one of the four biomarkers listed above, (c) obtaining a second urine sample from the subject 2 weeks to 12 months after the first urine sample is obtained, (d) determining in the second urine sample a level of the biomarker, and (e) assessing nephropathy progress in the subject. An increase in the level of the biomarker in the second urine sample, as compared to that in the first urine sample, indicates that nephropathy is exacerbated in the subject. When the subject is a human in early stage nephropathy, the second urine sample is obtained 6 to 12 months after the first urine sample is obtained. For a human subject in late stage nephropathy, the second urine sample can be obtained 3 to 6 months later than the first urine sample. When this method is applied to a laboratory animal, the second urine sample can be obtained 2 to 24 weeks after the first urine sample is obtained.

In still another aspect, the present invention provides a method for monitoring efficacy of a nephropathy treatment in a nephropathy patient, including (a) determining a level of one of the biomarkers listed above in a urine sample from the nephropathy patient before the treatment, (b) determining a level of the biomarker in a urine sample from the patient after the treatment, and (c) assessing efficacy of the treatment based on a change in the level of the biomarker after the treatment. The treatment is found to be effective when the post-treatment biomarker level remains the same or decreases as compared with the pre-treatment biomarker level.

This invention also provides a method of assessing renal toxicity of an agent, including (a) obtaining a plurality of urine samples from a subject treated with an agent at various time points during treatment, (b) determining in each of the urine samples a level of one of the above-described biomarkers, and (c) assessing renal toxicity of the agent based on a change in the level of the biomarker during the treatment. An increase in the biomarker level in the course of the treatment indicates that the agent is renal toxic. The agent can be a compound (e.g., a drug or a drug candidate), an herb product, and a food product This invention further provides a kit useful in any of the methods described above. This kit contains a first antibody specifically binding to leukocyte-associated Ig-like receptor-2 and a second antibody specifically binding to alpha-1 acid glycoprotein. Both antibodies can be whole immunoglobulin molecules. In one example, this kit contains only antibodies specific to antigens to be detected (e.g., biomarkers associated with nephropathy) for practicing one of the methods disclosed herein. Namely, it consists essentially of such antibodies.

Also within the scope of this invention is an isolated antibody specifically binding to DFLELLVKGTVPGTEAS-GFDAP (SEQ ID NO:1), or GQEHFAHLLILRDTKTYM-LAFDVNDEKNWGLS (SEQ ID NO:2). The term "isolated antibody" used herein refers to an antibody substantially free from naturally associated molecules. More specifically, a preparation containing the antibody is deemed as "an isolated antibody" when the naturally associated molecules in the preparation constitute at most 20% by dry weight. Purity can be measured by any appropriate method, e.g., column chromatography, polyacrylamide gel electrophoresis, and HPLC.

Any of the antibodies described above can be used in manufacturing a kit useful in practicing any of the methods of this invention.

The details of one or more embodiments of the invention are set forth in the description below. Other features or advantages of the present invention will be apparent from the following detailed description of several examples, and also from the appended claims.

BRIEF DESCRIPTION OF THE DRAWINGS

The drawings are first described.

DETAILED DESCRIPTION OF THE INVENTION

Figure 1:
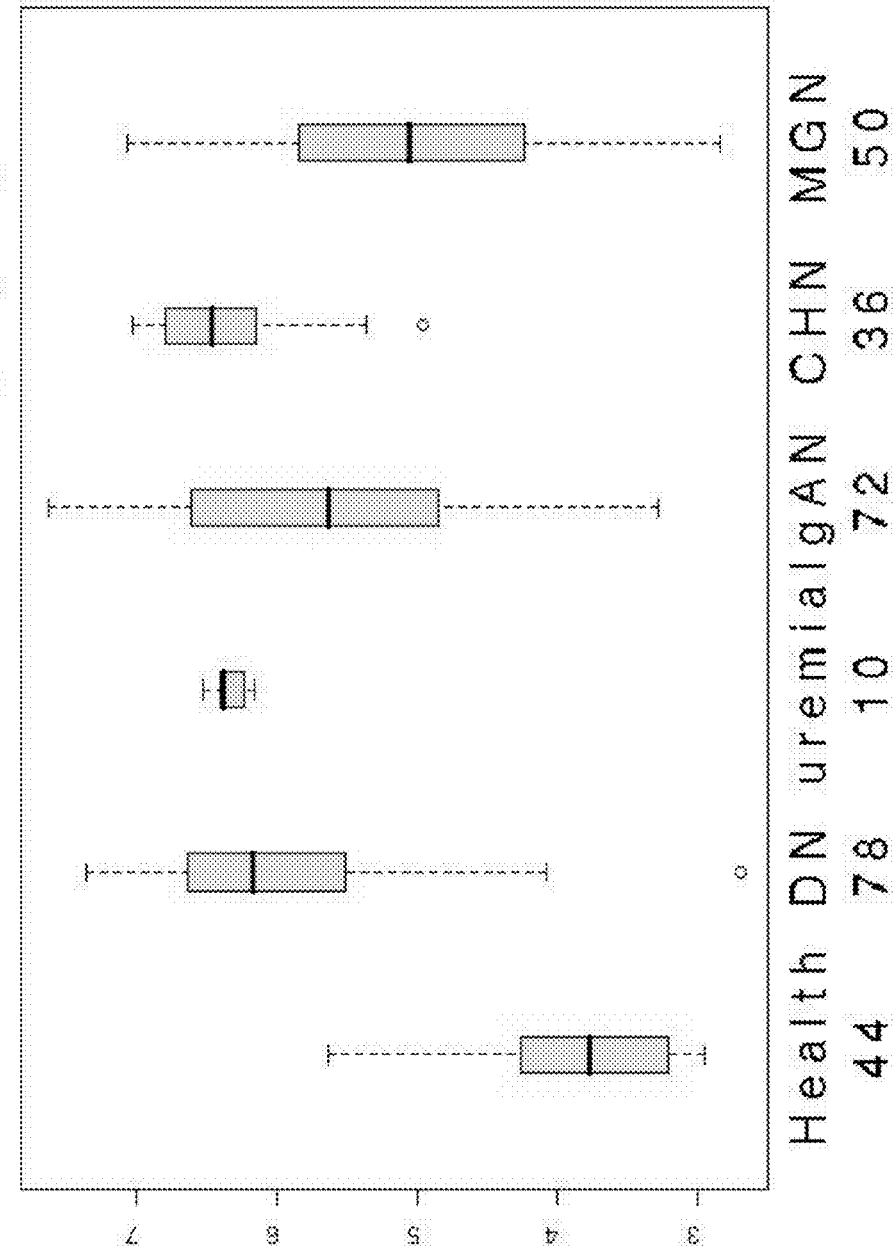
FIG. 1 is a diagram showing boxplots for combined levels of a fragment of leukocyte-associated Ig-like receptor-2 and a fragment of alpha-1 acid glycoprotein in healthy controls and patients having various types of nephropathy. DN, IgAN, CHN, and MGN refer to diabetic nephropathy, IgA nephropathy, Chinese herb nephropathy, and membranous glomerulonephritis nephropathy. The upper and lower limits of the boxes mark the 25% and 75% values with the medians as the lines across the boxes. The upper whisker marks the largest value below the upper fence, which is the 75% value plus 1.5 interquartile range and the lower whisker marks the smallest value above the lower fence, which is the 25% value minus 1.5 interquartile range.

In one aspect, the present invention relates to a method for diagnosing nephropathy based on the level of a urine biomarker, which can be leukocyte-associated Ig-like receptor-2 (GenBank accession number CAQ08962; 10 Jan. 2010), alpha-1 acid glycoprotein (GenBank accession number EAW87416; 10 Jan. 2010), a fragment of either protein, or a combination thereof. The fragment of either protein has a minimum length of ten amino acids and preferably, a maximum length of 120 to 200 amino acids. For example, fragments of leukocyte-associated Ig-like receptor-2 and alpha-1 acid glycoprotein can contain up to 125 and 191 amino acid residues, respectively. In one example, the fragment of leukocyte-associated Ig-like receptor-2 is DFLELLVKGTVPGTEASGFDAP (SEQ ID NO:1) and a fragment of alpha-1 acid glycoprotein is GQEHFAHLLIL-RDTKTYMLAFDVNDEKNWGLS (SEQ ID NO:2).

Each of the urine biomarkers mentioned above can be used to diagnose any type of nephropathy, including those related to diabetes (i.e., diabetic nephropathy), glomerulo-nephritis resulting from deposition of IgA in kidney tissues (i.e., IgA nephropathy), inflammation (e.g., membranous glomerulonephritis), Chinese herb-induced renal fibrosis (i.e., Chinese herbal nephropathy), chronic tubulointerstitial damage, which lead to renal failure (i.e., chronic interstitial nephritis), and focal segmental glomerulosclerosis.

To practice the diagnostic method of this invention, a urine sample is obtained from a subject suspected of having nephropathy and the level of any of the biomarkers mentioned above is then determined by conventional methods, e.g., ELISA and Western blot. When the biomarker is a peptide or a combination of peptides, its level can be determined by a mass spectrometry assay. The level of the urine biomarker can then be compared with a reference point representing the level of the same urine biomarker in a nephropathy-free subject. The reference point can be determined via routine practice based on the representative level of a urine biomarker in a group of nephropathy patients versus that in a group of nephropathy-free subjects. For example, it can be the middle point between the mean levels of these two groups. When the level of the urine biomarker in the subject is greater than the reference point, it indicates that the subject has nephropathy.

When necessary, patients having minimal change nephropathy (MCN) or minimal change disease (MCD) can be used as control groups for determining the reference point mentioned above. Generally, MCN and MCD patients exhibit obvious proteinuria but normal renal functions.

When a fragment of leukocyte-associated Ig-like receptor-2 or a fragment of alpha-1 acid glycoprotein is used, the diagnostic method of this invention can be applied to detect incipient nephropathy when presence of proteins (e.g., albumin) in urine is not detectable, i.e., free of proteinuria.

In another aspect, this invention relates to a method of monitoring nephropathy progress in a subject based on any of the urine biomarkers described above. To practice this method, two urine samples from a subject can be obtained within a suitable time span (e.g., 2 weeks to 12 months) and examined to determine the levels of one of the urine biomarkers described above. If the urine biomarker level in the later-obtained urine sample is greater than that in the earlier-obtained urine sample, it indicates that nephropathy progresses in the subject.

The monitoring method can be applied to a human subject suffering from or at risk for nephropathy. When the human subject is at risk for or in early stage nephropathy, the level of the urine biomarker can be determined once every 6 to 12 months to monitor nephropathy progress. When the human subject is already in late stage of nephropathy, it is preferred that the urine biomarker level be determined once every 3 to 6 months. While carrying kidney damage, patients in early stage nephropathy are generally asymptomatic and display normal kidney functions. These patients are at risk for nephropathy progress. Later stage nephropathy is characterized by a progressive decline in GFR (e.g., <15 mL/minute/1.73 $m^2$).

The monitoring method described above is also applicable a laboratory animal, following routine procedures, to study nephropathy. Preferably, the laboratory animal is examined once every 2 to 24 weeks to determine the level of one of the urine biomarkers mentioned above. An increase in the biomarker level over time indicates that the disease progresses in the animal.

In yet another aspect, the present invention provides a method for assessing efficacy of a nephropathy treatment in a subject in need (i.e., a human nephropathy patient or a laboratory animal bearing renal damage). In this method, the levels of one of the urine biomarkers described above are determined before, during, and/or after the treatment. If the urine biomarker level remains the same or decreases over the course of the treatment, it indicates that the treatment is effective.

Any of the urine biomarkers can also be used to monitor renal toxicity of a target agent, i.e., whether an agent induces renal damage. The target agent can be any compound or composition for human administration. Examples include, but are not limited to, chemical compounds, which can be drugs (e.g., non-steroidal anti-inflammatory drugs) or drug candidates, food products or supplements, and herb supplements. Renal toxicity of a target agent is indicated by its ability to increase the level of a urine biomarker over time.

Also disclosed herein is a kit useful in practicing any of the above-described methods. This kit contains at least two antibodies, one specific to Ig-like receptor-2, e.g., capable of binding to its fragment DFLELLVKGTVPGTEASGFDAP (SEQ ID NO:1) or any epitope contained therein, and the other specific to alpha-1 acid glycoprotein, e.g., capable of binding to its fragment GQEHFAHLLILRDTKTYMLAFD-VNDEKNWGLS (SEQ ID NO:2) or any epitope contained therein. In one example, the kit includes two different antibodies (i.e., a coating antibody and a detecting antibody) that bind to the same biomarker. Typically, the detecting antibody is conjugated with a molecule which emits a detectable signal either on its own or via binding to another agent. The term "antibody" used herein refers to a whole immunoglobulin or a fragment thereof, such as Fab or $F(ab')_2$ that retains antigen-binding activity. It can be naturally occurring or genetically engineered (e.g., single-chain antibody, chimeric antibody, or humanized antibody).

The antibodies included in the kit of this invention can be obtained from commercial vendors. Alternatively, they can be prepared by conventional methods. See, for example, Harlow and Lane, (1988) Antibodies: A Laboratory Manual, Cold Spring Harbor Laboratory, New York. To produce antibodies against a particular biomarker as listed above, the marker, optionally coupled to a carrier protein (e.g., KLH), can be mixed with an adjuvant, and injected into a host animal. Antibodies produced in the animal can then be purified by affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*. Polyclonal antibodies, i.e., heterogeneous populations of antibody molecules, are present in the sera of the immunized animal.

Monoclonal antibodies, i.e., homogeneous populations of antibody molecules, can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production.

Moreover, antibody fragments can be generated by known techniques. For example, such fragments include, but are not limited to, $F(ab')_2$ fragments that can be produced by pepsin digestion of an antibody molecule, and Fab fragments that can be generated by reducing the disulfide bridges of $F(ab')_2$ fragments.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

Example 1

Diagnosing Nephropathy Using Urine Leukocyte-Associated Ig-Like Receptor-2 or Alpha-1 Acid Glycoprotein as a Biomarker Material and Methods
(i) Subjects
  The following groups of human subjects were participated in this study:
  (a) healthy donors: free of diabetic mellitus with normal renal functions,
  (b) DM patients: having type 2 diabetic mellitus, but free from nephropathy,
  (c) DN patients: having diabetic nephropathy,
  (d) DN uremia patients: having DN associated with uremia,
  (e) IgAN patients: having IgA nephropathy,
  (f) MGN patients: having membranous glomerulonephritis,
  (g) CHN patients: having nephropathy induced by Chinese herb, and
  (h) CIN patients: having chronic interstitial nephritis.
Clinical characteristics of the healthy donors and the patients are summarized in Table 1 below:

TABLE 1

| | Patient Characteristics | | | | | | | |
|---|---|---|---|---|---|---|---|---|
| | Healthy | DM | DN | DN uremia | IgAN | MGN | CHN | CIN |
| Age, mean (SD) | 67.94 | 57.33 | 72.38 | 58.14 | 28.33 | 38.00 | 47.42 | 59.88 |
| | (12.30) | (10.52) | (7.44) | (12.79) | (12.31) | (13.11) | (10.43) | (7.62) |
| Female, n (%) | 6 | 2 | 1 | 2 | 4 | 2 | 14 | 4 |
| | (37.5) | (33.33) | (12.5) | (28.57) | (44.44) | (66.67) | (73.68) | (50.00) |

TABLE 1-continued

Patient Characteristics

|  | Healthy | DM | DN | DN uremia | IgAN | MGN | CHN | CIN |
|---|---|---|---|---|---|---|---|---|
| Serum Creatinine (mg/dL), mean (SD) | 0.86 (0.14) | 0.85 (0.24) | 1.39 (0.49) | 4.23 (4.65) | 1.03 (0.48) | 0.60 (0.20) | 5.39 (5.39) | 3.54 (2.28) |
| MDRD_S_GFR, mean (SD) | 86.28 (13.19) | 106.86 (70.47) | 58.60 (20.75) | 58.02 (61.53) | 104.29 (56.19) | 144.96 (55.15) | 22.70 (17.07) | 24.32 (15.91) |

(ii) MALDI-MS Assay

Midstream urinary samples were collected from the groups of human subjects listed above in early morning. These urine samples from both healthy donors and patients, mixed with protease inhibitors, were analyzed by MALDI-TOF-MS. Peptide candidates that were differentially presented in the healthy donor group and the various patient groups were identified upon comparison of polypeptide patterns between each patient group and the healthy donor group, taking into consideration statistical evaluation of demographic and sample parameters. These peptides were purified, their amino acid sequences determined via routine technology.

(Iii) Western Blot Assay

Western blotting analysis was performed using antibodies specific to leukocyte-associated Ig-like receptor-2 fragment DFLELLVKGTVPGTEASGFDAP (SEQ ID NO:1) and alpha-1 acid glycoprotein fragment GQEHFAHLLILRDT-KTYMLAFDVNDEKNWGLS (SEQ ID NO:2), following routine technology. The results were normalized against the level of creatinine or protein in the same sample.

(iv) ELISA

Urine samples were mixed with protease inhibitors and diluted at 1:100 with a dilution buffer and serum samples were diluted at 1:10. The diluted samples were placed in ELISA plates in triplicates. The concentrations of leukocyte-associated Ig-like receptor-2 and alpha-1 acid glycoprotein were determined via the standard sandwich ELISA method and normalized against the level of creatinine or protein in the same sample.

Results

Via the MALDI-MS assay described above, peptides DFLELLVKGTVPGTEASGFDAP (SEQ ID NO:1) and GQEHFAHLLILRDTKTYMLAFDVNDEKNWGLS (SEQ ID NO:2) were detected in urine samples from nephropathy patients at much higher levels as compared to urine samples from healthy controls. SEQ ID NOs:1 and 2 are fragments of leukocyte-associated Ig-like receptor-2 and alpha-1 acid glycoprotein, respectively. The positive rates of these two peptides in the healthy donor group and in the various patient groups are shown in Table 2 below:

TABLE 2

| Categories | Groups | Patient Numbers | Positive rates of SEQ ID NO: 2 N (%) | Positive rates of SEQ ID NO: 1 N (%) |
|---|---|---|---|---|
| Healthy | Health | 19 | 0 (0%) | 1 (5.3%) |
| Diabetic | DM | 7 | 0 (0%) | 2 (28.6%) |
| Nephropathy | DN | 8 | 2 (25%) | 8 (100%) |
|  | DN uremia | 11 | 6 (54.5%) | 8 (72.7%) |
| Immune-mediated Nephropathy | IgAN | 12 | 0 (0%) | 8 (66.7%) |
|  | MGN | 3 | 0 (0%) | 2 (66.7%) |
| Interstitial Nephritis | CHN | 18 | 10 (55.6%) | 17 (94.4%) |
|  | CIN | 7 | 3 (42.9%) | 7 (100%) |
| Total |  | 85 | 21 | 53 |

The results also show that the urine levels of these two peptides in nephropathy patients were not correlated with proteinuria, indicating that they can be used to detect kidney lesions prior to the appearance of proteins, particularly albumin, in urine.

Further, the urine levels of these two peptides in nephropathy patients were found to exhibit reverse correlations with GFR, indicating that they can serve as markers for monitoring renal function changes and nephropathy progress.

Via the ELISA and Western blot assays described above, leukocyte-associated Ig-like receptor-2 and alpha-1 acid glycoprotein were found to be differentially presented in urine samples from nephropathy patients (e.g., patients having Chinese herb-induced nephropathy) versus urine samples from healthy controls. See Table 3 below. More specifically, presence of either protein in urine samples from healthy controls was barely detectable; while a higher level of the protein was found in urine samples from nephropathy patients. This result indicates that either protein can be used as a marker for diagnosing nephropathy.

TABLE 2

Ratios of Alpha-1 Acid Glycoprotein to Creatinine in Various Patient Groups

|  | Healthy | DM | DN | IgAN | MGN | CHN | CIN | DN uremia |
|---|---|---|---|---|---|---|---|---|
| AGP/Cr (ng/mg) × 1000 mean (SD) | 2.57 (2.52) | 2.91 (1.68) | 29.18 (30.93) | 15.52 (20.87) | 139.51 (137.53) | 19.55 (39.36) | 51.31 (65.46) | 97.13 (140.60) |

Example 2

Diagnosing Nephropathy Using the Combination of Leukocyte-Associated Ig-Like Receptor-2 and Alpha-1 Acid Glycorprotein as a Biomarker The levels of urine leukocyte-associated Ig-like receptor-2 and alpha-1 acid glycorprotein from both healthy controls and nephropathy patients (including patients having diabetic nephropathy, uremia, IgA nephropathy, Chinese herb-induced nephropathy, and membranous glomerulonephritis nephropathy) were determined as described in Example 1 above.

As shown in FIG. 1, the combined level of the above-mentioned two protein markers was much higher in all types of nephropathy patients as compared to that in healthy controls (AUROC=0.93). This indicates that leukocyte-associated Ig-like receptor-2 and alpha-1 acid glycorprotein, in combination, can be used as a reliable biomarker for diagnosing nephropathy with high sensitivity and specificity.

Figure 2:
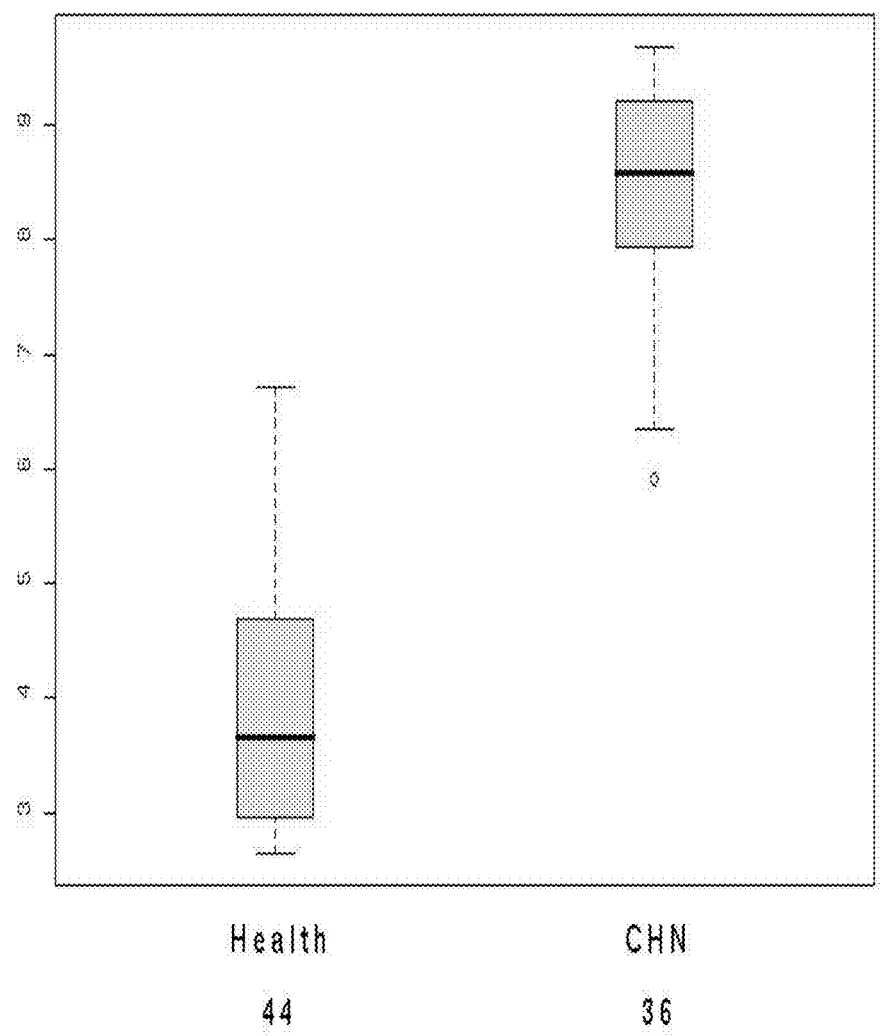
FIG. 2 is a diagram showing boxplots for combined levels of a fragment of leukocyte-associated Ig-like receptor-2 and a fragment of alpha-1 acid glycoprotein in healthy controls and patients having CHN. The upper and lower limits of the boxes mark the 25% and 75% values with the medians as the lines across the boxes. The upper whisker marks the largest value below the upper fence, which is the 75% value plus 1.5 interquartile range and the lower whisker marks the smallest value above the lower fence, which is the 25% value minus 1.5 interquartile range.

The combination of urine leukocyte-associated Ig-like receptor-2 and alpha-1 acid glycorprotein was found to be particularly reliable in detecting nephropathy induced by Chinese herb. See FIG. 2. The AUROC obtained from this study reaches 1.0, indicating that the diagnosing accuracy is 100% when using this biomarker in diagnosing patients having Chinese herb-induced nephropathy.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

---

---

What is claimed is:

1. A method of detecting, in a urine sample, the level of a fragment of leukocyte-associated Ig-like receptor-2 consisting of the sequence of SEQ ID NO:1, wherein the detecting step is performed with an immune assay.

2. The method of claim 1, wherein the immune assay is Western blot, ELISA, radioimmunoassay (RIA), fluorescent immunoassay (FIA), or luminescence immunoassay (LIA).

3. The method of claim 1, wherein the urine sample is obtained from a human subject.

4. The method of claim 1, wherein the urine sample is obtained from a laboratory animal.

* * * * *